(12) United States Patent
Oh

(10) Patent No.: US 9,766,061 B2
(45) Date of Patent: Sep. 19, 2017

(54) APPARATUS AND METHOD FOR MEASURING PRETILT ANGLE OF LIQUID CRYSTAL

(71) Applicant: Samsung Display Co., Ltd., Yongin, Gyeonggi-Do (KR)

(72) Inventor: Sejoon Oh, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 52 days.

(21) Appl. No.: 14/704,136

(22) Filed: May 5, 2015

(65) Prior Publication Data

US 2016/0146596 A1 May 26, 2016

(30) Foreign Application Priority Data

Nov. 25, 2014 (KR) .................... 10-2014-0165503

(51) Int. Cl.
*G01B 11/26* (2006.01)
*G01N 21/21* (2006.01)
(Continued)

(52) U.S. Cl.
CPC ............. *G01B 11/26* (2013.01); *G01N 21/21* (2013.01); *G02F 1/1309* (2013.01);
(Continued)

(58) Field of Classification Search
CPC .... G02F 1/1309; G02F 1/1393; G02F 1/1337; G02F 1/133753; G02F 2001/133746;
(Continued)

(56) References Cited

U.S. PATENT DOCUMENTS

| 5,612,450 A | * 3/1997 | Mizushima ....... G02F 1/133723 349/123 |
| 6,348,966 B1 | 2/2002 | Hirosawa |

(Continued)

FOREIGN PATENT DOCUMENTS

| JP | 06074864 A | * 3/1994 |
| JP | 08094445 A | * 4/1996 |

(Continued)

OTHER PUBLICATIONS

Kitamura, Michio et al., "Accurate determination of pretilt angle in twisted-nematic liquid-crystal cells by using a rotating analyzer," 2006, Journal of the SID 14/5, pp. 509-514.*

(Continued)

*Primary Examiner* — Gordon J Stock, Jr.
(74) *Attorney, Agent, or Firm* — H.C. Park & Associates, PLC

(57) ABSTRACT

An apparatus and method for measuring a pretilt angle of a liquid crystal (LC) are disclosed. The method includes irradiating polarized light on an LC cell including a first substrate, a second substrate facing the first substrate, and an LC layer between the first substrate and the second substrate. At least one of the first substrate and the second substrate includes a minute branch electrode. Irradiated light is scanned within a predetermined angle range in a direction not parallel to the minute branch electrode, an intensity of light that is transmitted through the LC cell is detected, and a pretilt angle of the LC is obtained by using a light intensity detection signal corresponding to the transmitted light.

14 Claims, 6 Drawing Sheets

(51) Int. Cl.
*G02F 1/13* (2006.01)
*G02F 1/1337* (2006.01)
*G02F 1/139* (2006.01)

(52) U.S. Cl.
CPC . *G01N 2021/214* (2013.01); *G01N 2021/218* (2013.01); *G02F 1/1337* (2013.01); *G02F 1/1393* (2013.01); *G02F 2001/133746* (2013.01); *G02F 2001/133749* (2013.01); *G02F 2001/133773* (2013.01)

(58) Field of Classification Search
CPC ........ G02F 2001/133749; G02F 2001/133761; G02F 2001/133773; G01B 11/26; G01N 21/21; G01N 2021/218; G01N 2021/214; G01J 4/00; G01J 9/00
USPC .................................................. 356/364–370
See application file for complete search history.

(56) References Cited

U.S. PATENT DOCUMENTS

| | | | |
|---|---|---|---|
| 7,855,787 B2* | 12/2010 | Rossini | G02F 1/1309 349/118 |
| 2001/0019390 A1 | 9/2001 | Itoh et al. | |
| 2003/0071995 A1 | 4/2003 | Kurata et al. | |
| 2005/0046771 A1 | 3/2005 | Lee et al. | |
| 2006/0290855 A1 | 12/2006 | Itoh et al. | |
| 2009/0109387 A1* | 4/2009 | Sakai | G02F 1/133734 349/124 |
| 2009/0296089 A1* | 12/2009 | Smith | G01B 11/0641 356/367 |
| 2011/0242468 A1* | 10/2011 | Choi | C08G 8/12 349/129 |
| 2013/0258262 A1* | 10/2013 | Lee | G02F 1/133707 349/123 |

FOREIGN PATENT DOCUMENTS

| | | | |
|---|---|---|---|
| JP | 2001-356072 A | | 12/2001 |
| JP | 2002311406 A | * | 10/2002 |
| JP | 2004-028710 A | | 1/2004 |
| JP | 4895428 B2 | * | 3/2012 |
| KR | 1999-0062629 A | | 7/1999 |
| KR | 10-2010-0048907 A | | 5/2010 |
| KR | 10-2010-0099662 A | | 9/2010 |

OTHER PUBLICATIONS

Nishioka, Takahiro et al., "Novel Pretilt Angle Measurement Method for Twisted-Nematic Liquid-Crystal Cells by Apparent Retardation Measurement," Oct. 2001, Japanese Journal of Applied Physics, vol. 40, Part I, No. 10, pp. 6017-6023.*

Wang, Sheng-Ya et al., "Simple method to obtain accurate pretilt angles for thin twisted nematic liquid-crystal cells," Jan. 10, 2013, Applied Optics, vol. 52, No. 2, pp. 219-225.*

* cited by examiner

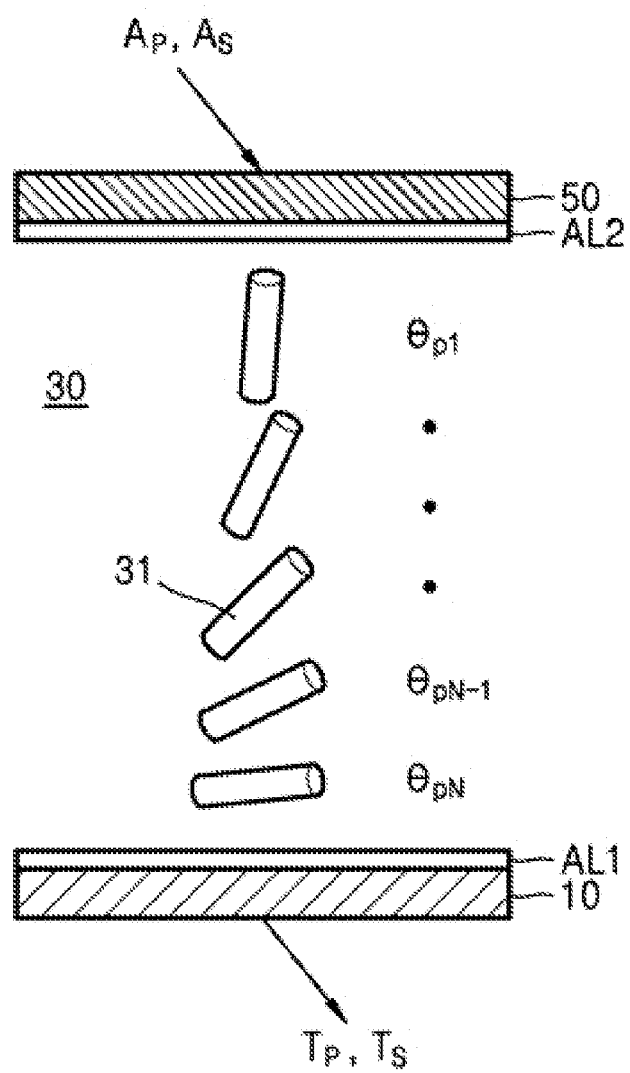

APPARATUS AND METHOD FOR MEASURING PRETILT ANGLE OF LIQUID CRYSTAL

CLAIM OF PRIORITY

This application claims all benefits accruing under 35 U.S.C. §119 from an Korean Patent Application No. 10-2014-0165503, filed on Nov. 25, 2014, in the Korean Intellectual Property Office, the disclosure of which is incorporated herein in its entirety by reference.

BACKGROUND OF THE INVENTION

Field of the Invention

One or more exemplary embodiments of the present invention relate to an apparatus and method for measuring a pretilt angle of a liquid crystal (LC).

Description of the Related Art

An LC cell used in liquid crystal display (LCD) devices generally includes a lower substrate, an upper substrate facing the lower substrate, and an LC layer between the lower substrate and the upper substrate.

As the lower substrate is a display substrate, a plurality of data lines and a plurality of gate lines, which define a plurality of pixel regions, are arranged on the lower substrate, switching elements, such as a thin-film transistor, are arranged in regions where the plurality of data lines and the plurality of gate lines cross each other, and pixel electrodes are located in pixel regions. A color filter may be disposed, for example, under the upper substrate.

To improve the display performance of an LCD device, LC molecules are initially oriented to make a predetermined angle with a substrate surface. The initial orientation angle of an LC molecule is referred to as a pretilt angle.

Since the display performance of the LCD device depends on the pretilt angles, the pretilt angles need to be detected.

SUMMARY OF THE INVENTION

One or more exemplary embodiments of the present invention include an apparatus and method for measuring a pretilt angle of a liquid crystal (LC), whereby the pretilt angle of the LC is separately measured for each of two substrates forming an LC cell.

Additional aspects will be set forth in part in the description which follows and, in part, will be apparent from the description, or may be learned by practice of the presented embodiments of the present invention.

According to one or more exemplary embodiments of the present invention, a method of measuring a pretilt angle of a liquid crystal (LC) includes: irradiating polarized light on an LC cell including a first substrate, a second substrate facing the first substrate, and an LC layer between the first substrate and the second substrate, wherein at least one of the first substrate and the second substrate includes a minute branch electrode; scanning the irradiated polarized light within a predetermined angle range in a direction not parallel to the minute branch electrode; detecting an intensity of light that is transmitted through the LC cell; and obtaining a pretilt angle of the LC based on a light intensity detection signal corresponding to the transmitted irradiated polarized light.

The scanning of the irradiated polarized light may be performed in a direction crossing the minute branch electrode.

The obtaining of the pretilt angle of the LC may include detecting an amplitude and a phase difference of the transmitted light, calculating a Jones matrix based on the obtained amplitude and phase difference, obtaining a change in the Jones matrix through scanning of the irradiated polarized light, and determining the pretilt angle of the LC by using the change in the Jones matrix.

Non-diagonal components of the Jones matrix may not be zero.

The pretilt angle of the LC may be separately obtaining for each of the first substrate and the second substrate.

A thin-film transistor switching element may be disposed on one of the first substrate and the second substrate, a color filter may be disposed on other one of the first substrate and the second substrate, and an alignment layer may be provided on opposite surfaces of the first substrate and the second substrate.

According to one or more exemplary embodiments of the present invention, an apparatus for measuring a pretilt angle of a liquid crystal (LC) includes: a light source unit configured to irradiate light on an LC cell including a first substrate, a second substrate facing the first substrate, and an LC layer between a first substrate and a second substrate, wherein at least one of the first substrate and the second substrate includes a minute branch electrode, and to scan the irradiated light within a predetermined angle range in a direction not parallel to the minute branch electrode; a polarizer configured to polarize the light so that polarized light irradiates on the LC cell; an optical detector configured to detect an intensity of light transmitted through the LC cell; and a signal processing unit configured to obtain a pretilt angle of the LC by using a light intensity detection signal corresponding to the transmitted light.

The light source unit may be further configured to scan the light in a direction that crosses the minute branch electrode.

The signal processing unit may be further configured to calculate a Jones matrix based on an amplitude and a phase difference of the transmitted light, obtaining a change in the Jones matrix, and determining the pretilt angle of the LC based on the change in the Jones matrix.

Non-diagonal components of the Jones matrix may not be zero.

The signal processing unit may be further configured to separately measure the pretilt angle for each of the first substrate and the second substrate.

A thin-film transistor switching element may be disposed on one of the first substrate and the second substrate, a color filter may be disposed on another one of the first substrate and the second substrate, and an alignment layer may be provided on opposite surfaces of the first substrate and the second substrate.

BRIEF DESCRIPTION OF THE DRAWINGS

These and/or other aspects will become apparent and more readily appreciated from the following description of the exemplary embodiments of the present invention, taken in conjunction with the accompanying drawings in which:

FIG. 6 illustrates an LC layer of the LC cell, which is divided into N layers, LC tilt angles of which are represented as $\theta_{p1}, \ldots, \theta_{pN-1}, \theta_{pN}$;

DETAILED DESCRIPTION OF THE INVENTION

Figure 1:
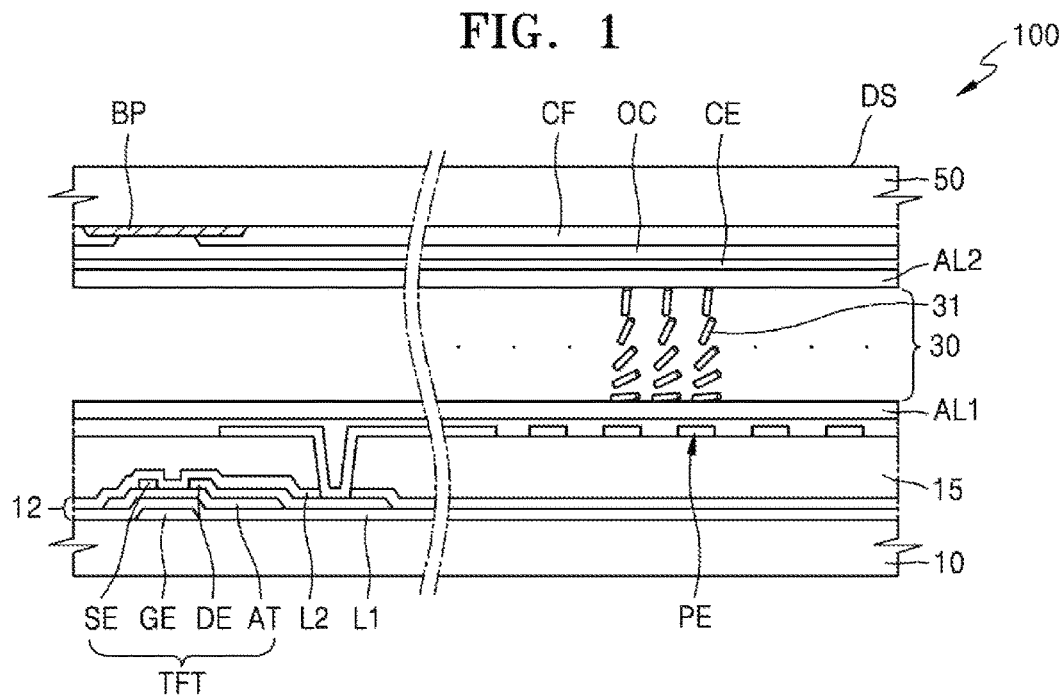
FIG. 1 is a cross-sectional view of a liquid crystal (LC) cell of a liquid crystal display (LCD) device.

Reference will now be made in detail to exemplary embodiments of the present invention, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments of the present invention are merely described below by referring to the figures to explain aspects of the present description.

It will be understood that, although the terms "first", "second", etc. may be used herein to describe various components, these components should not be limited by these terms. These components are only used to distinguish one component from another.

As used herein, the singular forms "a," "an" and "the" are intended to include the plural forms as well unless the context clearly indicates otherwise.

It will be further understood that the terms "comprises" and/or "comprising" used herein specify the presence of stated features or components, but do not preclude the presence or addition of one or more other features or components.

It will be understood that, when a layer, region, or component is referred to as being "formed on," another layer, region, or component, it can be directly or indirectly formed on the other layer, region, or component. That is, for example, intervening layers, regions, or components may be present.

Sizes of elements in the drawings may be exaggerated for convenience of explanation. In other words, since sizes and thicknesses of components in the drawings are arbitrarily illustrated for convenience of explanation, the following embodiments of the present invention are not limited thereto.

When a certain embodiment of the present invention may be implemented differently, a specific process order may be performed differently from the described order. For example, two consecutively described processes may be performed substantially at the same time or performed in an order opposite to the described order.

As used herein, expressions such as "at least one of," when preceding a list of elements, modify the entire list of elements and do not modify the individual elements of the list.

Figure 2:
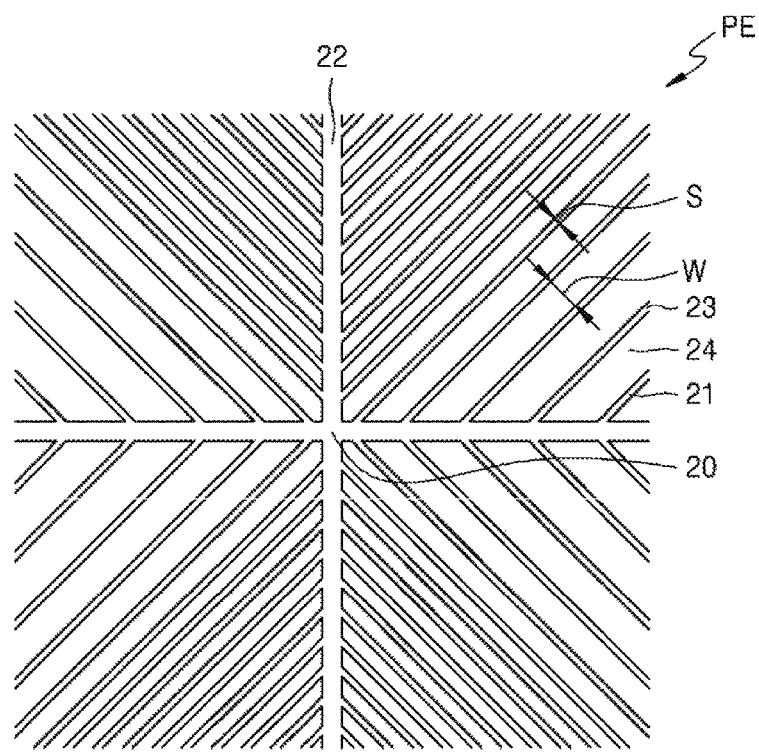
FIG. 2 is a top view of an exemplary shape of a pixel electrode applied to the LC cell of FIG. 1.

FIG. 1 is a cross-sectional view of a liquid crystal (LC) cell of a liquid crystal display (LCD) device, and FIG. 2 is a top view of an example shape of a pixel electrode applied to the LC cell of FIG. 1.

Referring to FIG. 1, the LC cell 100 includes a first substrate 10, a second substrate 50, and a liquid crystal (LC) layer 30. An LC 31 of the LC layer 30 may be oriented such that the LC 31 has a predetermined pretilt angle with each of the first substrate 10 and the second substrate 50. To form the pretilt angle, a first alignment layer AL1 may be formed on an opposite surface of the first substrate 10, and a second alignment layer AL2 may be formed on an opposite surface of the second substrate 50. In the LC cell 100, the first and second substrates 10 and 50, respectively, may be assembled so as to be facing each other and the first and second alignment layers AL1 and AL2 are formed on the opposing surfaces of the first and second substrates 10 and 50, respectively.

A thin-film transistor array layer 12 and a pixel electrode PE are formed on the opposite surface of the first substrate 10. The thin-film transistor array layer 12 includes a plurality of switching elements TFT, a plurality of gate lines (not shown), and a plurality of data lines (not shown).

The first substrate 10 may be a glass substrate or a plastic substrate including polyethylene terephthalate (PET), polyethylene naphthalate (PEN), polyimide, or the like.

The switching element TFT is a thin-film transistor and includes an active layer AT, a gate electrode GE, a source electrode SE, and a drain electrode DE.

A first insulating layer L1, which is a gate insulating layer, is formed on the gate electrode GE, the active layer AT is formed on the first insulating layer L1. The drain electrode DE and the source electrode SE are formed on the active layer AT such that the drain electrode DE and the source electrode SE are spaced apart from each other, and a second insulating layer L2 covering the drain electrode DE and the source electrode SE is formed.

The active layer AT may be formed to include various materials. For example, the active layer AT may include an inorganic semiconductor material such as amorphous silicon or crystalline silicon. As another example, the active layer AT may include an oxide semiconductor. As another example, the active layer AT may include an organic semiconductor material.

The gate electrode GE, the source electrode SE, and the drain electrode DE may be formed of at least one metal selected from the group consisting of aluminum (Al), platinum (Pt), palladium (Pd), silver (Ag), magnesium (Mg), gold (Au), nickel (Ni), neodymium (Nd), iridium (Ir), chromium (Cr), lithium (Li), calcium (Ca), molybdenum (Mo), titanium (Ti), tungsten (W), and copper (Cu), and in a single layer or multiple layers.

The first insulating layer L1 and the second insulating layer L2 may be formed of various types of insulating materials. The first insulating layer L1 and the second insulating layer L2 may be formed of at least one insulating layer selected from the group consisting of silicon oxide ($SiO_2$), silicon nitride ($SiN_x$), silicon oxynitride (SiON), aluminum oxide ($Al_2O_3$), titanium oxide ($TiO_2$), tantalum oxide ($Ta_2O_5$), hafnium oxide ($HfO_2$), zirconium oxide (ZrO$_2$), barium stronium titanate (BST), and Lead Zirconate Titanate (PZT), and in a single layer or multiple layers.

A planarization layer 15 may be further provided on the thin-film transistor array layer 12.

The pixel electrode PE is provided on the planarization layer 15 and is connected to the drain electrode DE of the switching element TFT by passing through the planarization layer 15 and the second insulating layer L2.

The first alignment layer AL1 is further formed on the pixel electrode PE so that the LC 31 is pretilted with respect to the first substrate 10.

A light-blocking pattern BP, a color filter CF, an overcoating layer OC, and a common electrode CE may be formed on the opposite surface of the second substrate 50, and the second alignment layer AL2 may be formed on the common electrode CE. The second substrate 50 may be a glass substrate or a transparent plastic substrate, and an outer surface of the second substrate 50 becomes a display surface DS.

The light-blocking pattern BP may be disposed on the opposite surface of the second substrate 50 at a location corresponding to a region in which the switching element TFT, a gate line (not shown), and a data line (not shown) are formed, and blocks light. The disposition location of the light-blocking pattern BP is only illustrative, and the light-blocking pattern BP may alternatively be disposed on the opposite surface of the first substrate 10.

The color filter CF is disposed on the opposite surface of the second substrate 50 and filters colored light. The disposition of the color filter CF is only illustrative, and the color filter CF may be disposed on the opposite surface of the first substrate 10.

The overcoating layer OC is disposed on the second substrate 50 on which the color filter CF has been formed and planarizes the opposite surface of the second substrate 50. The overcoating layer OC may be omitted.

The common electrode CE is disposed on the opposite surface of the second substrate 50 such that the common electrode CE faces the pixel electrode PE, and a reference voltage, i.e., a common voltage, which defines the polarity of a voltage to be applied to the pixel electrode PE, is applied to the common electrode CE. The common electrode CE may have a flat plate shape. The common electrode CE may also have a patterned electrode shape.

The pixel electrode PE may have the shape as shown in FIG. 2. Referring to FIG. 2, the pixel electrode PE includes a cross-shaped stem part 20, wherein the cross-shaped stem part 20 includes a horizontal stem part 21 and a vertical stem part 22. A plurality of minute branch electrodes 23 are formed extending obliquely from the horizontal stem part 21 and the vertical stem part 22. A pixel region may be partitioned into four domains by the cross-shaped stem part 20.

Although the minute branch electrode 23 is shown in a straight line shape, the shape may be modified to a zigzag shape. Although a width S of the minute branch electrode 23 and a width W of a minute slit 24 between the minute branch electrodes 23 are shown constant, the widths S and W may be modified differently and may be properly designed in consideration of an LC control force, a texture decrease, and the like.

In an initial orientation state in which no voltage is applied between the common electrode CE and the pixel electrode PE, the LC 31 of the LC layer 30 may form a first pretilt angle $\theta_t$ at a location adjacent to the first alignment layer AL1 and may form a second pretilt angle $\theta_c$ at a location adjacent to the second alignment layer AL2.

Although the LC cell 100 and the pixel electrode PE, for which an LC pretilt angle may be measured by an apparatus and method for measuring a pretilt angle of an LC according to one or more embodiments of the present invention, have been described with reference to FIGS. 1 and 2, an LC cell to which the apparatus and method for measuring a pretilt angle of an LC according to one or more embodiments of the present invention are applied is not limited thereto, and an LC pretilt angle may be measured for LC cells having minute branch electrodes of various structures. Hereinafter, although reference numerals of a first substrate, a second substrate, an alignment layer, a minute branch electrode, a minute slit, and the like are the same as those in FIGS. 1 and 2, it should not be understood that the use of the same reference numerals limits application examples of an LC cell having a minute branch electrode to FIGS. 1 and 2, and it should be understood that the same reference numerals are used for convenience of description.

Figure 3:
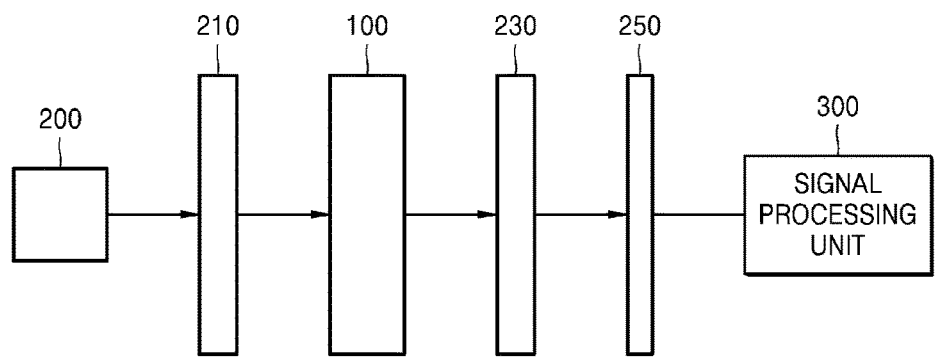
FIG. 3 illustrates an apparatus for measuring a pretilt angle of an LC according to an embodiment of the present invention.
Figure 4:
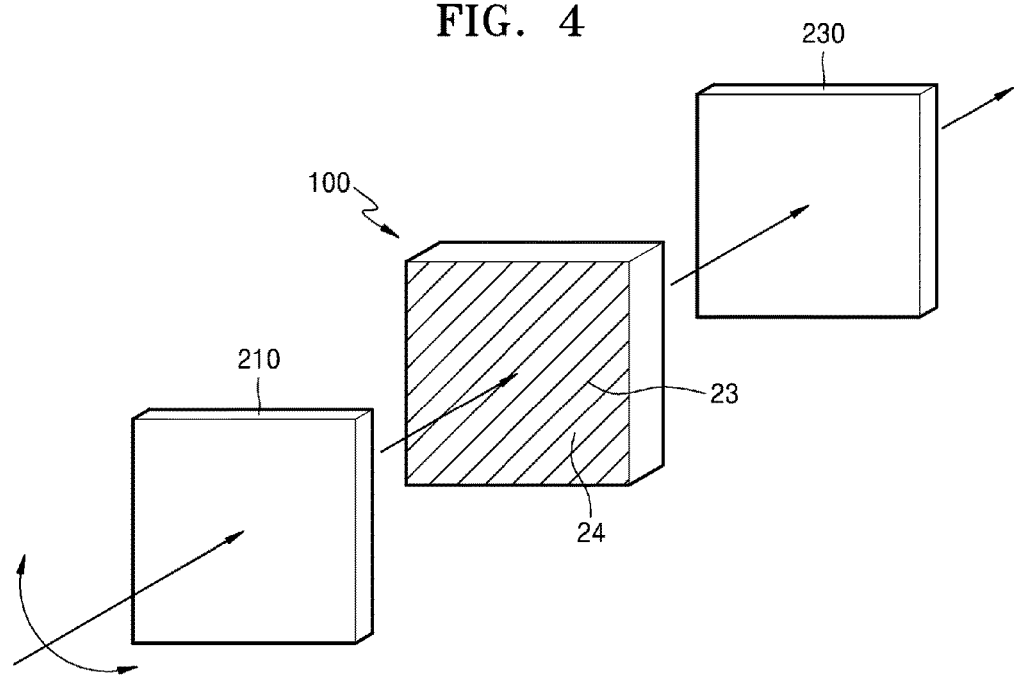
FIG. 4 is a perspective view showing a relationship between a scan direction of incident light and a minute branch electrode (minute slit) of the LC cell in the apparatus of FIG. 3.

FIG. 3 illustrates an apparatus for measuring a pretilt angle of an LC according to an embodiment of the present invention, and FIG. 4 is a perspective view showing a relationship between a scan direction of incident light and the minute branch electrode (minute slit) of the LC cell in the apparatus of FIG. 3.

Referring to FIGS. 3 and 4, the apparatus of FIG. 3 may be provided to irradiate polarized light on the LC cell 100, to scan the irradiated light within a predetermined angle range in a direction which is not parallel to the minute branch electrode 23 of the LC cell 100, e.g., a direction crossing the minute branch electrode 23, so as to detect the intensity of light which has transmitted through the LC cell 100 and to obtain a pretilt angle of the LC 31 by using a light intensity detection signal of the transmitted light. That is, the apparatus of FIG. 3 may include a light source unit 200 and a polarizer 210 in front of the LC cell 100, may include an analyzer 230 and an optical detector 250 at the rear of the LC cell 100, and may include a signal processing unit 300 for calculating the pretilt angle of the LC 31 by using the light intensity detection signal of the transmitted light detected by the optical detector 250.

In the LC cell 100, as described above with reference to FIGS. 1 and 2, an electrode formed on one of the first and second substrates 10 and 50, respectively, e.g., the pixel electrode PE formed on the first substrate 10, may include the minute branch electrode 23. When the minute branch electrode 23 is included, the LC 31 may be aligned along the minute branch electrode 23. In a structure in which a polarizer and an analyzer are coupled to the LC cell 100, the polarizer 210 and the analyzer 230 may be omitted.

The light source unit 200 may be provided to irradiate light on the LC cell 100 while scanning the irradiated light within a predetermined angle range in a direction which is not parallel to the minute branch electrode 23. The light source unit 200 may include, for example, a light source for emitting light and a scanner for scanning the light emitted from the light source within a predetermined range. The light source unit 200 may be provided to, for example, irradiate light on the LC cell 100 while scanning the irradiated light in a direction crossing the minute branch electrode 23.

The polarizer 210 polarizes the light provided from the light source unit 200 such that the polarized light, e.g., linearly polarized light, is irradiated on the LC cell 100. The polarizer 210 may be located between the light source unit 200 and the LC cell 100, or may be located between the light source and the scanner when the light source unit 200 includes the light source and the scanner. Herein, since the light source unit 200 is shown as a block in FIG. 3, FIG. 3 shows that the polarizer 210 is located between the light source unit 200 and the LC cell 100. The analyzer 230 may be provided to, for example, pass only polarized light which is orthogonal to the light polarized by the polarizer 210. The optical detector 250 detects the intensity of light which has transmitted through the LC cell 100.

The signal processing unit 300 (i.e. signal processor) is driven to obtain a pretilt angle of the LC 31 by using a light intensity detection signal of the transmitted light. The signal processing unit 300 calculates a Jones matrix by obtaining an amplitude and a phase difference of the transmitted light and determines the pretilt angle of the LC 31 by obtaining a change in the Jones matrix through the light scanning.

The light irradiated on the LC cell 100 is scanned in a direction which is not parallel to the minute branch electrode 23, e.g., a direction crossing the minute branch electrode 23.

Figure 5:
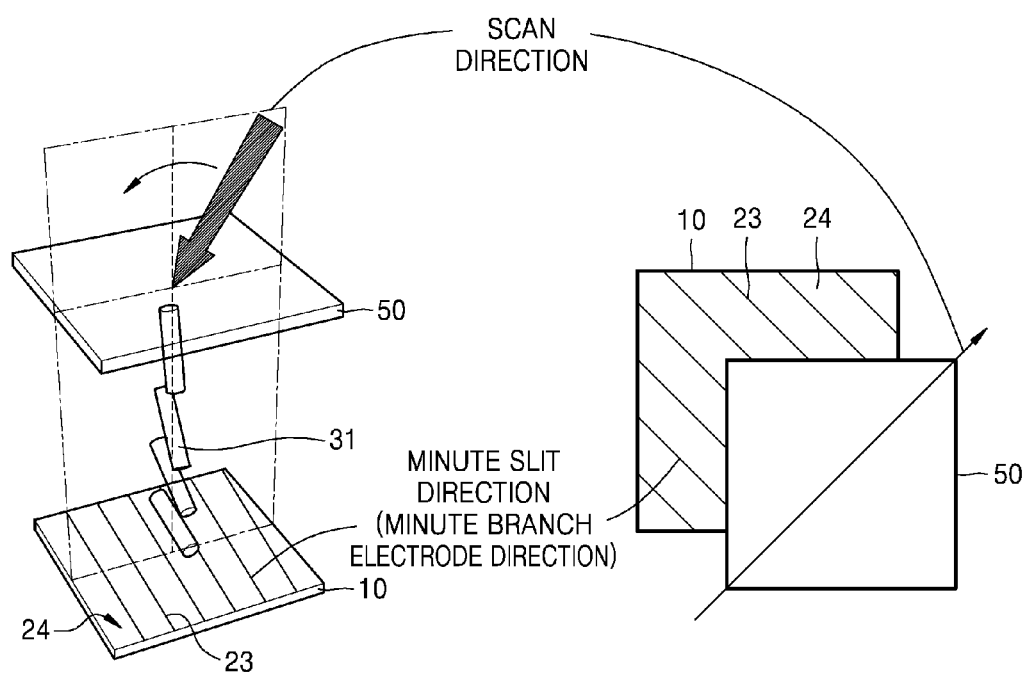
FIG. 5 illustrates a relationship between a minute branch electrode direction (minute slit direction) and a scan direction of incident light with respect to an incident plane when the incident light is scanned in a direction crossing the minute branch electrode.

FIG. 5 illustrates a relationship between a minute branch electrode direction (minute slit direction) and a scan direction of incident light with respect to an incident plane when the incident light is scanned in a direction crossing the minute branch electrode 23. As shown in FIG. 5, the minute slit 24 is formed between the minute branch electrodes 23, and the light incident to the LC cell 100 may be scanned in the direction which is not parallel to the minute branch electrode 2, e.g., a direction crossing the minute branch electrode 23. Herein, an incident angle range of the scanned incident light may be, for example, a range between approximately −30° to approximately 30° or more.

As described above, when the light irradiated on the LC cell 100 is scanned in the direction which is not parallel to the minute branch electrode 23, matrix coefficients of non-diagonal components of the Jones matrix are not zero, and accordingly, the pretilt angle of the LC 31 may be separately detected for each of the first substrate 10 and the second substrate 50. Herein, the direction of scanning of the light irradiated on the LC cell 100 may be a direction in which the matrix coefficients of the non-diagonal components of the Jones matrix are maximized, e.g., the direction crossing the minute branch electrode 23.

FIG. 6 illustrates the LC layer of the LC cell, which is divided into N layers, LC tilt angles of which are represented as $\theta_{p1}, \ldots, \theta_{pN-1}, \theta_{pN}$.

Referring to FIG. 6, when incident light is incident on the LC cell 100, if it is assumed that a p-polarization component of the incident light is $A_p$, an s-polarization component of the incident light is $A_s$, a p-polarization component of transmitted light which has transmitted through the LC cell 100 is $T_p$, and an s-polarization component of the transmitted light is $T_s$, a relationship between $(A_p, A_s)$ and $(T_p, T_s)$ may be represented by an extended Jones matrix method, i.e., Equation 1:

$$\begin{pmatrix} T_P \\ T_S \end{pmatrix} = \underbrace{\begin{pmatrix} t_{epN} & t_{opN} \\ t_{esN} & t_{osN} \end{pmatrix} \begin{pmatrix} e^{-i\delta_{eV}} & 0 \\ 0 & e^{-i\delta_{oN}} \end{pmatrix} \begin{pmatrix} t_{eeN-1} & t_{oeN-1} \\ t_{eoN-1} & t_{ooN-1} \end{pmatrix} \ldots \begin{pmatrix} t_{ee1} & t_{oe1} \\ t_{eo1} & t_{oo1} \end{pmatrix} \begin{pmatrix} e^{-i\delta_{e1}} & 0 \\ 0 & e^{-i\delta_{o1}} \end{pmatrix} \begin{pmatrix} t_{pe0} & t_{se0} \\ t_{po0} & t_{so0} \end{pmatrix}}_{\text{Jones Matrix}} \begin{pmatrix} A_P \\ A_S \end{pmatrix} \quad (1)$$

In Equation 1, $t_{eo}$ denotes a transmission matrix coefficient represented by a function of an LC twist angle, and $\delta$ denotes a phase delay.

By calculating a Jones matrix predicted according to pretilts of LCs 31 and comparing the calculated Jones matrix with a Jones matrix obtained by measuring transmitted light, the pretilt angles $\theta_{p1}, \ldots, \theta_{pN-1}, \theta_{pN}$ of the LCs 31 may be determined.

The Jones matrix may be represented by, for example, Equation 2.

$$\begin{pmatrix} A_{11} & A_{12} \\ A_{21} & A_{22} \end{pmatrix} \quad (2)$$

In this case, the matrix coefficients of the diagonal components of the Jones matrix are $A_{11}$ and $A_{22}$, and the matrix coefficients of the non-diagonal components of the Jones matrix are $A_{12}$ and $A_{21}$.

When incident light is perpendicularly incident to the LC cell 100, the LCs 31 are not twisted, and thus, the Jones matrix is a diagonal matrix. In this case, the matrix coefficients of the diagonal components of the Jones matrix have non-zero values, but the matrix coefficients of the non-diagonal components of the Jones matrix are zero. That is, in Equation 2, the matrix coefficients $A_{11}$ and $A_{22}$ of the diagonal components have non-zero values, but the matrix coefficients $A_{12}$ and $A_{21}$ of the non-diagonal components are zero.

Equation 3 represents an extended Jones matrix when the Jones matrix is a diagonal matrix, as follows:

$$\begin{pmatrix} T_P \\ T_S \end{pmatrix} = \begin{pmatrix} t_{epN} & 0 \\ 0 & t_{osN} \end{pmatrix} \begin{pmatrix} e^{-i\delta_{eV}} & 0 \\ 0 & e^{-i\delta_{oN}} \end{pmatrix} \begin{pmatrix} t_{eeN-1} & 0 \\ 0 & t_{ooN-1} \end{pmatrix} \ldots \quad (3)$$

As shown in Equation 3, when matrix coefficients of non-diagonal components of each Jones matrix of the extended Jones matrix are zero, that is, when the Jones matrix is a diagonal matrix because the LCs 31 are not twisted, an exchange law is satisfied, and thus, an optical characteristic only depends on the phase delay δ, and accordingly, even though the first pretilt angle $\theta_t$ at a surface of the first substrate 10 and the second pretilt angle $\theta_c$ at a surface of the second substrate 50 are exchanged with each other, distinction of the first pretilt angle $\theta_t$ and the second pretilt angle $\theta_c$ is not possible.

However, according to the present embodiment, when incident light is scanned and incident to the LC cell 100 in a direction which is not parallel to the minute branch electrode 23, e.g., a direction crossing the minute branch electrode 23, the Jones matrix is not a diagonal matrix. In this case, not only the matrix coefficients of the diagonal components but also the matrix coefficients of the non-diagonal components of the Jones matrix have non-zero values. That is, in Equation 2, the matrix coefficients $A_{11}$ and $A_{22}$ of the diagonal components have non-zero values, and the matrix coefficients $A_{12}$ and $A_{21}$ of the non-diagonal components may also have non-zero values instead of zero.

Equation 4 represents an extended Jones matrix when the Jones matrix is not a diagonal matrix, as follows:

$$\begin{pmatrix} T_P \\ T_S \end{pmatrix} = \begin{pmatrix} t_{epN} & t_{opN} \\ t_{esN} & t_{osN} \end{pmatrix} \begin{pmatrix} e^{-i\delta_{eV}} & 0 \\ 0 & e^{-i\delta_{oN}} \end{pmatrix} \begin{pmatrix} t_{eeN-1} & t_{oeN-1} \\ t_{eoN-1} & t_{ooN-1} \end{pmatrix} \ldots \quad (4)$$

As shown in Equation 4, when matrix coefficients of non-diagonal components of each Jones matrix of the extended Jones matrix exist, an exchange law is not satisfied because the Jones matrix is not a diagonal matrix, and thus, the first pretilt angle $\theta_t$ at the surface of the first substrate 10 and the second pretilt angle $\theta_c$ at the surface of the second substrate 50 may be discriminated from each other.

Figure 7A:
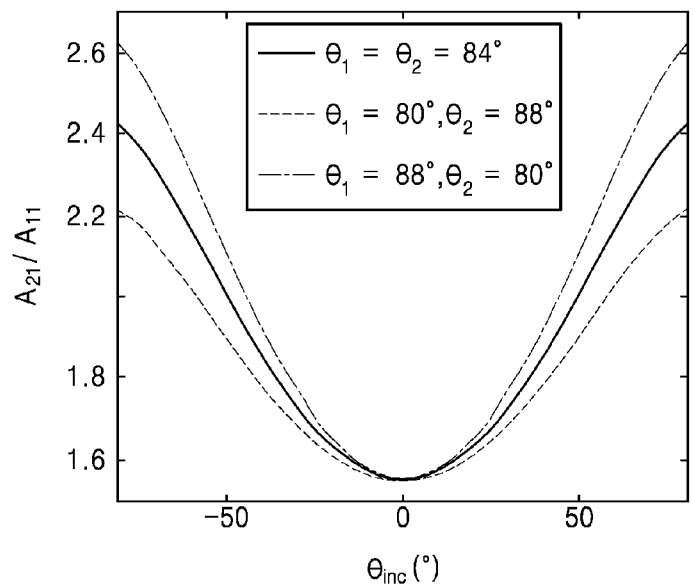
FIGS. 7A and 7B are graphs showing a change in a ratio of a matrix coefficient of a diagonal component of a Jones matrix to a matrix coefficient of a non-diagonal component of the Jones matrix according to an incident angle of light irradiated on the LC cell when the light is scanned in a direction crossing the minute branch electrode (minute slit)
Figure 7B:
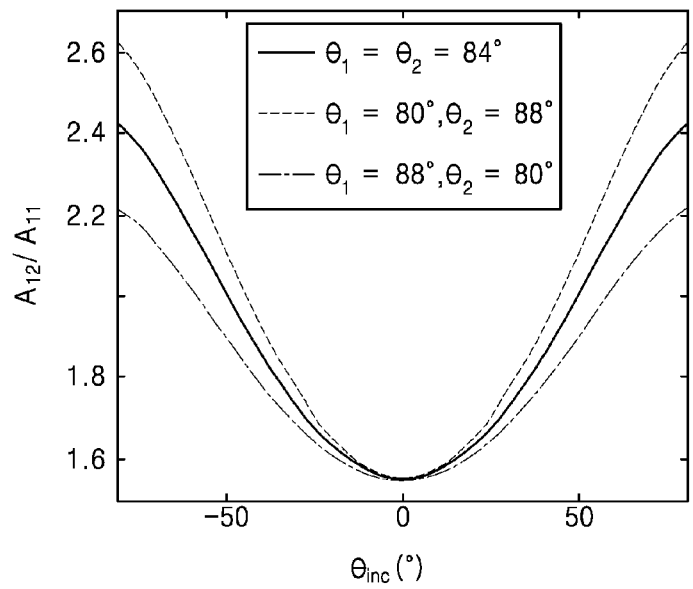

FIGS. 7A and 7B are graphs showing a change in a ratio of a matrix coefficient of a diagonal component of a Jones matrix to a matrix coefficient of a non-diagonal component of the Jones matrix according to an incident angle of light irradiated on the LC cell 100 when the light is scanned in a direction crossing the minute branch electrode 23 (minute slit 24). In FIGS. 7A and 7B, $\theta_1$ may denote any one of the first pretilt angle $\theta_t$ at the surface of the first substrate 10 and the second pretilt angle $\theta_c$ at the surface of the second substrate 50, and $\theta_2$ may denote the other one thereof.

In FIG. 7A, the vertical axis indicates a ratio of the matrix coefficient $A_{21}$ to the matrix coefficient $A_{11}$ of the Jones matrix, and in FIG. 7B, the vertical axis indicates a ratio of the matrix coefficient $A_{12}$ to the matrix coefficient $A_{11}$ of the Jones matrix. In FIGS. 7A and 7B, the horizontal axis indicates an incident angle $\theta_{inc}$ of light incident to the LC cell 100.

As shown in FIGS. 7A and 7B, ratios of matrix coefficients according to an incident angle are different from each other when $\theta_1=\theta_2=84°$, when $\theta_1=80°$ and $\theta_2=84°$, and when $\theta_1=88°$ and $\theta_2=80°$.

Therefore, when light incident on the LC cell 100 is scanned in a direction which is not parallel to the minute branch electrode 23, a Jones matrix is not a diagonal matrix, and not only matrix coefficients of diagonal components but also matrix coefficients of non-diagonal components of the Jones matrix exist, and thus, the first pretilt angle $\theta_t$ at to the surface of the first substrate 10 and the second pretilt angle $\theta_c$ at the surface of the second substrate 50, may be separately determined.

Figure 8A:
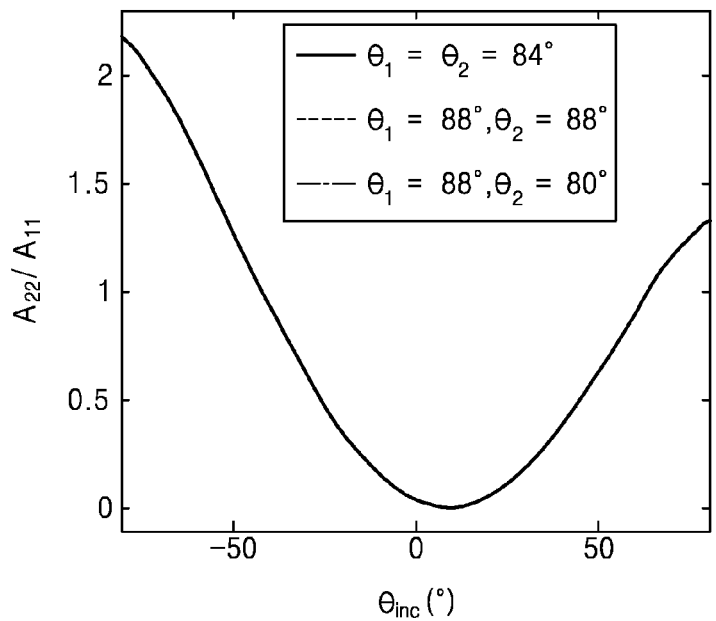
FIGS. 8A and 8B are graphs showing, as a comparison example, a change in a ratio of two matrix coefficients of diagonal components of a Jones matrix according to an incident angle of light irradiated on the LC cell when the light is scanned in the front direction and a direction which is parallel to the minute branch electrode.
Figure 8B:
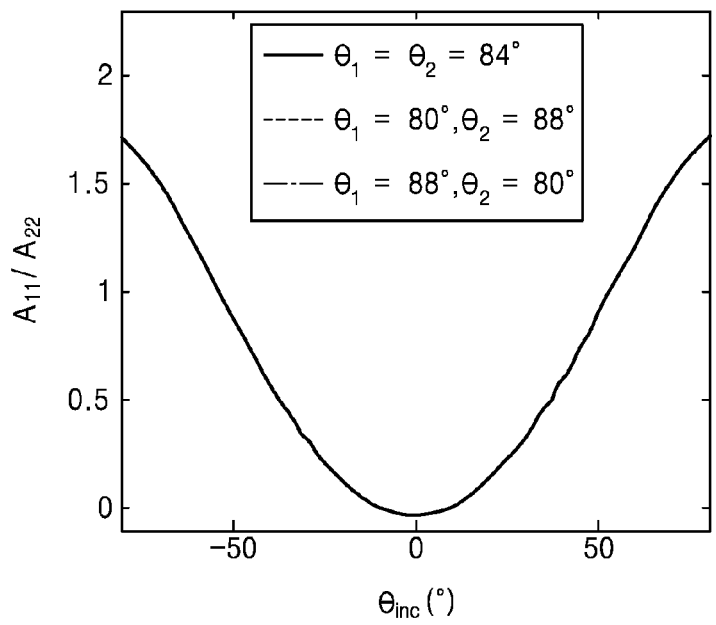

As a comparison example, FIGS. 8A and 8B are graphs showing a change in a ratio of two matrix coefficients of diagonal components of a Jones matrix according to an incident angle of light irradiated on the LC cell 100 when the light is scanned in the front direction and a direction which is parallel to the minute branch electrode 23. When the light incident to the LC cell 100 is scanned in a direction which is parallel to the minute branch electrode 23, the Jones matrix is a diagonal matrix, and thus only the matrix coefficients of the diagonal components of the Jones matrix have non-zero values, and matrix coefficients of non-diagonal components of the Jones matrix are zero.

In FIG. 8A, the vertical axis indicates a ratio of the matrix coefficient $A_{22}$ to the matrix coefficient $A_{11}$ of the diagonal components of the Jones matrix, and in FIG. 8B, the vertical axis indicates a ratio of the matrix coefficient $A_{11}$ to the matrix coefficient $A_{22}$ of the diagonal components of the Jones matrix. In FIGS. 8A and 8B, the horizontal axis indicates an incident angle $\theta_{inc}$ of light incident on the LC cell 100.

As shown in FIGS. 8A and 8B, ratios of matrix coefficients according to an incident angle are the same as each other when $\theta_1=\theta_2=84°$, when $\theta_1=80°$ and $\theta_2=84°$, and when $\theta_1=88°$ and $\theta_2=80°$. When this comparison example is applied, the first pretilt angle $\theta_t$ at the surface of the first substrate 10 and the second pretilt angle $\theta_c$ at the surface of the second substrate 50 cannot be discriminated from each other, and even though the first pretilt angle $\theta_t$ and the second pretilt angle $\theta_c$ are exchanged, the exchange cannot be identified.

As described above, according to an apparatus and method for measuring a pretilt angle of an LC according to the one or more of the above exemplary embodiments of the present invention, since the intensity of light which has transmitted through an LC cell is detected while scanning light irradiated on the LC cell having a minute branch electrode in a direction which is not parallel to the minute branch electrode, and a pretilt angle is produced by using the detected light intensity, the pretilt angle of the LC may be separately obtained for each of two substrates.

It should be understood that the exemplary embodiments of the present invention described therein should be considered in a descriptive sense only and not for purposes of limitation. Descriptions of features or aspects within each exemplary embodiment of the present invention should typically be considered as available for other similar features or aspects in other exemplary embodiments of the present invention.

While one or more exemplary embodiments of the present invention have been described with reference to the figures, it will be understood by those of ordinary skill in the art that various changes in form and detail may be made therein without departing from the spirit and scope of the present invention as defined by the following claims.

What is claimed is:

1. A method of measuring a pretilt angle of a liquid crystal (LC), the method comprising the steps of:
   irradiating polarized light on an LC cell including a first substrate, a second substrate facing the first substrate, and an LC layer between the first substrate and the second substrate, wherein at least one of the first substrate and the second substrate includes a minute branch electrode;
   scanning the irradiated polarized light within a predetermined angle range in a direction not parallel to the minute branch electrode;
   detecting an intensity of light that is transmitted through the LC cell; and
   obtaining separately a pretilt angle of the LC for each of the first substrate and the second substrate by using a light intensity detection signal corresponding to the transmitted light.

2. The method of claim 1, wherein the scanning of the irradiated polarized light is performed in a direction crossing the minute branch electrode.

3. The method of claim 1, wherein a thin-film transistor switching element is disposed on one of the first substrate and the second substrate, a color filter is disposed on another one of the first substrate and the second substrate, and an alignment layer is provided at opposite surfaces of the first substrate and the second substrate.

4. The method of claim 1, the predetermined angle range being in the range of approximately −30° to approximately 30° from being perpendicularly incident to the LC cell.

5. The method of claim 1, wherein the step of obtaining the pretilt angle of the LC for each of the first substrate and the second substrate comprises detecting an amplitude and a phase difference of the transmitted light, creating a Jones matrix based on the detected amplitude and phase difference, obtaining a change in the Jones matrix through scanning of the irradiated polarized light, and determining the pretilt angle of the LC for each of the first substrate and the second substrate by using the change in the Jones matrix.

6. The method of claim 5, wherein non-diagonal components of the Jones matrix are not zero.

7. An apparatus for measuring a pretilt angle of a liquid crystal (LC), the apparatus comprising:
   a light source unit irradiating light on an LC cell including a first substrate, a second substrate facing the first substrate, and an LC layer between the first substrate and the second substrate, wherein at least one of the first substrate and the second substrate includes a minute branch electrode, the irradiated light being scanned within a predetermined angle range in a direction not parallel to the minute branch electrode;

a polarizer polarizing the light so that polarized light irradiates on the LC cell;

an optical detector detecting an intensity of light transmitted through the LC cell; and a signal processor separately measuring a pretilt angle of the LC for each of the first substrate and the second substrate by using a light intensity detection signal corresponding to the transmitted light.

8. The apparatus of claim 7, wherein the light source unit scans the light in a direction that crosses the minute branch electrode.

9. The apparatus of claim 7, wherein a thin-film transistor switching element is disposed on one of the first substrate and the second substrate, a color filter is disposed on another one of the first substrate and the second substrate, and an alignment layer is provided on opposite surfaces of the first substrate and the second substrate.

10. The apparatus of claim 7, the predetermined angle range being in the range of approximately −30° to approximately 30°.

11. The apparatus of claim 7, wherein the signal processor creates a Jones matrix based on an amplitude and a phase difference of the transmitted light, obtains a change in the Jones matrix, and determines the pretilt angle of the LC for each of the first substrate and the second substrate based on the change in the Jones matrix.

12. The apparatus of claim 11, wherein non-diagonal components of the Jones matrix are not zero.

13. An apparatus for measuring a pretilt angle of a liquid crystal (LC), the apparatus comprising:

a light source unit irradiating light on an LC cell including a first substrate, a second substrate facing the first substrate, and an LC layer between the first substrate and the second substrate, wherein at least one of the first substrate and the second substrate includes a minute branch electrode, the irradiated light being scanned within a predetermined angle range in a direction not parallel to the minute branch electrode;

a polarizer polarizing the light so that polarized light irradiates on the LC cell an optical detector detecting an intensity of light transmitted through the LC cell; and a signal processor determining a pretilt angle of the LC for each of the first and second substrates by using a light intensity detection signal corresponding to the transmitted light.

14. The apparatus of claim 13, wherein the signal processor also:

calculating a Jones matrix based on an amplitude and a phase difference of the transmitted light;

obtaining a change in the Jones matrix; and determining the pretilt angle of the LC for each of the first and the second substrates based on the change in the Jones matrix.

* * * * *